(12) United States Patent
DeBates et al.

(10) Patent No.: US 10,819,837 B2
(45) Date of Patent: Oct. 27, 2020

(54) MOBILE DEVICE WITH VOC MONITORING OF USER BREATH AND ENVIRONMENT

(71) Applicant: Motorola Mobility LLC, Chicago, IL (US)

(72) Inventors: Scott DeBates, Crystal Lake, IL (US); Douglas Lautner, Round Lake, IL (US); Daryl C. Cromer, Chicago, IL (US); George Standish, Chicago, IL (US); Nigil George Valikodath, Chicago, IL (US)

(73) Assignee: Motorola Mobility LLC, Chicago, IL (US)

( * ) Notice: Subject to any disclaimer, the term of this patent is extended or adjusted under 35 U.S.C. 154(b) by 0 days.

(21) Appl. No.: 15/906,581

(22) Filed: Feb. 27, 2018

(65) Prior Publication Data

US 2019/0268458 A1    Aug. 29, 2019

(51) Int. Cl.
| | | |
|---|---|---|
| *H04M 1/21* | (2006.01) | |
| *A61B 5/08* | (2006.01) | |
| *A61B 5/00* | (2006.01) | |
| *G01N 33/497* | (2006.01) | |
| *A61B 5/097* | (2006.01) | |

(52) U.S. Cl.
CPC ............... *H04M 1/21* (2013.01); *A61B 5/082* (2013.01); *A61B 5/097* (2013.01); *A61B 5/6898* (2013.01); *G01N 33/497* (2013.01); *A61B 2562/0247* (2013.01); *G01N 2033/4975* (2013.01); *H04M 2250/12* (2013.01)

(58) Field of Classification Search
CPC ..... H04M 1/21; H04M 2250/12; A61B 5/082; A61B 5/097; A61B 5/6898; A61B 2562/0247; G01N 33/497; G01N 2033/4975
See application file for complete search history.

(56) References Cited

U.S. PATENT DOCUMENTS

| | | | |
|---|---|---|---|
| 2012/0157871 A1* | 6/2012 | Walden | A61B 5/097 600/532 |
| 2014/0335905 A1* | 11/2014 | Bhoot | H04W 4/02 455/466 |
| 2015/0182146 A1* | 7/2015 | Hidaka | G01N 33/497 455/418 |
| 2016/0202224 A1* | 7/2016 | Lloyd | G01N 33/0016 73/865.8 |
| 2017/0318135 A1* | 11/2017 | Han | G08B 21/14 |
| 2017/0318136 A1* | 11/2017 | Han | H04M 1/0202 |
| 2018/0074081 A1* | 3/2018 | Wakana | G01N 33/98 |

* cited by examiner

*Primary Examiner* — Yuwen Pan
*Assistant Examiner* — Angelica M Perez
(74) *Attorney, Agent, or Firm* — McKinney Philips LLC; Phillip Pippenger (57) ABSTRACT

Systems and methods for user exhalation and environmental air analysis are implemented in an integrated or dockable analysis architecture including an opening adjacent a device microphone to admit an exhalation of a user while the user is speaking. In an embodiment, the opening leads to a passageway having at least one gas sensor therein, located such that a user exhalation entering the opening will impinge on the at least one gas sensor. A processor is linked to the gas sensor, and is configured to receive sensor signals from the gas sensor and generate biological information for the user.

11 Claims, 8 Drawing Sheets

MOBILE DEVICE WITH VOC MONITORING OF USER BREATH AND ENVIRONMENT

TECHNICAL FIELD

The present disclosure is related generally to mobile electronic communications devices and, more particularly, to systems and methods for verifying or enhancing user wellness information via a mobile electronic communications device.

BACKGROUND

A person's health and well-being can be sensed or inferred from various biological parameters. These include, for example, heart rate, blood pressure, glucose level, and so on. Typically, biological parameter measurements are intrusive, even if not invasive. For example, a person interested in one or more of their biological parameters related to health must typically visit a health care practitioner or obtain and use a specialized medical device. This makes it inconvenient to check such parameters, and thus reduces a person's desire and ability to be aware of their health.

Before proceeding to the remainder of this disclosure, it should be appreciated that the disclosure may address some of the shortcomings listed or implicit in this Background section. However, any such benefit is not a limitation on the scope of the disclosed principles, or of the attached claims, except to the extent expressly noted in the claims.

Additionally, the discussion of technology in this Background section is reflective of the inventors' own observations, considerations, and thoughts, and is in no way intended to be, to accurately catalog, or to comprehensively summarize any prior art reference or practice. As such, the inventors expressly disclaim this section as admitted or assumed prior art. Moreover, the identification or implication herein of one or more desirable courses of action reflects the inventors' own observations and ideas, and should not be assumed to indicate an art-recognized desirability.

BRIEF DESCRIPTION OF THE SEVERAL VIEWS OF THE DRAWINGS

While the appended claims set forth the features of the present techniques with particularity, these techniques, together with their objects and advantages, may be best understood from the following detailed description taken in conjunction with the accompanying drawings of which:

DETAILED DESCRIPTION

Before presenting a detailed discussion of embodiments of the disclosed principles, an overview of certain embodiments is given to aid the reader in understanding the later discussion. As noted above, it is often inconvenient for users to check biological parameters related to their health. For example, a person's breath may be analyzed to make medical findings and inferences regarding the person's health. However, a person interested in such analysis must typically obtain and use multiple devices, e.g., for personal VOC (Volatile Organic Compound) analysis as well as environmental VOC analysis.

In an embodiment of the described principles, a system is provided for seamlessly monitoring a person's emitted VOC when the person is speaking into a mobile electronic communication device. The same system may also monitor the VOC's in the user's environment. The system may be integrated into the device, e.g., via gas sensors embedded with the device speech microphone assembly, or may be in the form of an add-on device such as a MOTOROLA MOD, that is usable with one or more typed of cellular device. Additional and alternative features will become more apparent below.

With this overview in mind, and turning now to a more detailed discussion in conjunction with the attached figures, the techniques of the present disclosure are illustrated as being implemented in or via a suitable device environment. The following device description is based on embodiments and examples within which or via which the disclosed principles may be implemented, and should not be taken as limiting the claims with regard to alternative embodiments that are not explicitly described herein.

Figure 1:
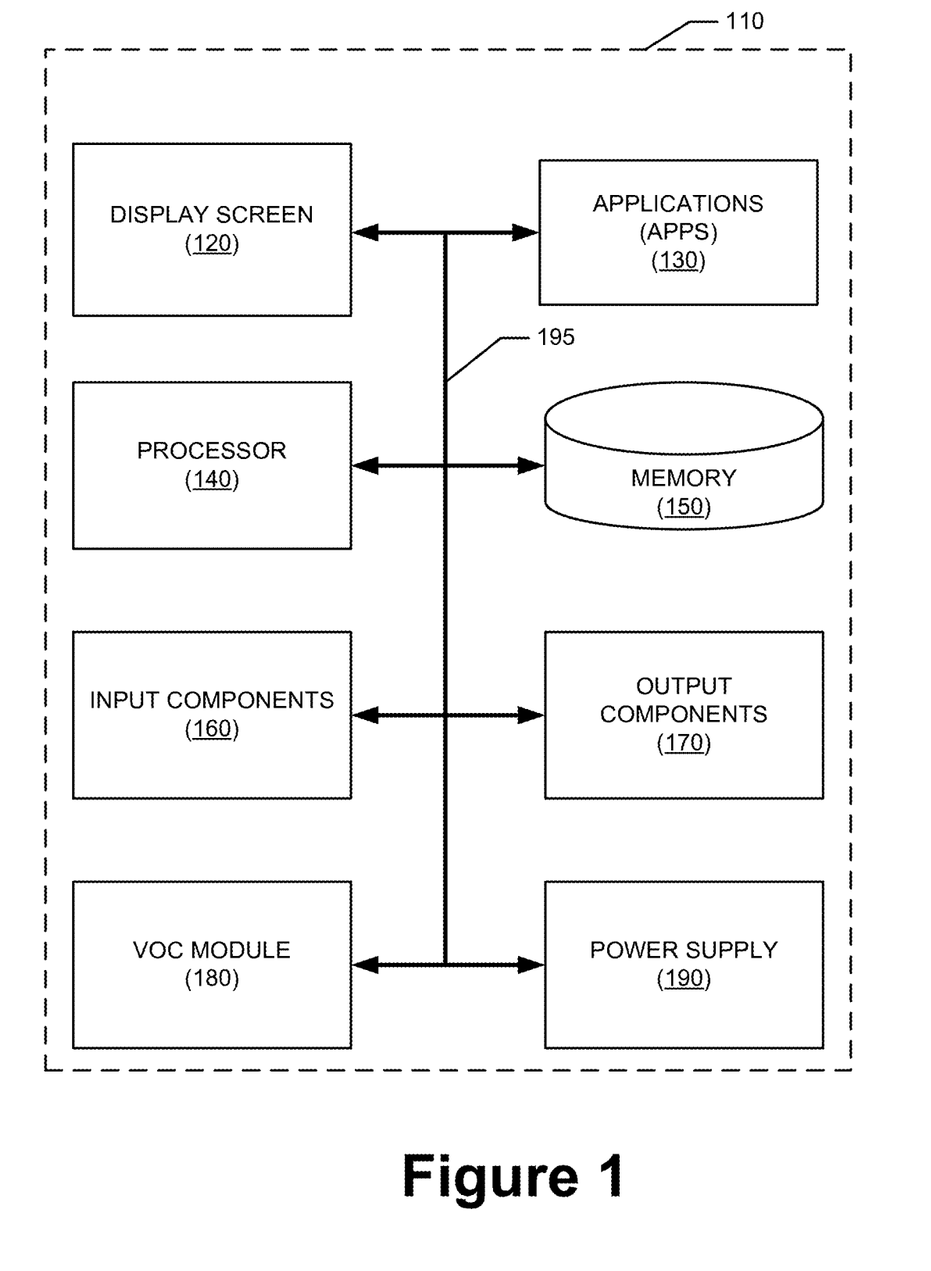
FIG. 1 is a general schematic representation of a mobile electronic device in which various embodiments of the disclosed principles may be implemented.

Thus, for example, while FIG. 1 illustrates an example mobile electronic communications device with respect to which embodiments of the disclosed principles may be implemented, it will be appreciated that other device types may be used, including but not limited to laptop computers, tablet computers, and so on. It will be appreciated that additional or alternative components may be used in a given implementation depending upon user preference, component availability, price point and other considerations.

In the illustrated embodiment, the components of the user device 110 include a display screen 120, applications (e.g., programs) 130, a processor 140, a memory 150, one or more input components 160 such as RF input facilities or wired input facilities, including, for example one or more antennas and associated circuitry and logic. The antennas and associated circuitry may support any number of protocols, e.g., WiFi, Bluetooth, cellular, etc.

The device 110 as illustrated also includes one or more output components 170 such as RF (radio frequency) or wired output facilities. The RF output facilities may similarly support any number of protocols, e.g., WiFi, Bluetooth, cellular, etc., and may be the same as or overlapping with the associated input facilities. It will be appreciated that a single physical input may serve for both transmission and receipt.

The processor 140 can be any of a microprocessor, microcomputer, application-specific integrated circuit, and the like. For example, the processor 140 can be implemented by one or more microprocessors or controllers from any desired family or manufacturer. Similarly, the memory 150 is a nontransitory media that may reside on the same integrated circuit as the processor 140. Additionally or alternatively, the memory 150 may be accessed via a network, e.g., via cloud-based storage. The memory 150 may include a random access memory (i.e., Synchronous Dynamic Random Access Memory (SDRAM), Dynamic Random Access Memory (DRAM), RAMBUS Dynamic Random Access Memory (RDRM) or any other type of random access memory device or system). Additionally or alternatively, the memory 150 may include a read-only memory (i.e., a hard drive, flash memory or any other desired type of memory device).

The information that is stored by the memory 150 can include program code associated with one or more operating systems or applications as well as informational data, e.g., program parameters, process data, etc. The operating system and applications are typically implemented via executable instructions stored in a non-transitory computer readable medium (e.g., memory 150) to control basic functions of the electronic device 110. Such functions may include, for example, interaction among various internal components and storage and retrieval of applications and data to and from the memory 150.

Further with respect to the applications and modules such as a VOC module 180, these typically utilize the operating system to provide more specific functionality, such as file system service and handling of protected and unprotected data stored in the memory 150. In an embodiment, the VOC module 180 is a software agent that includes or interacts with hardware components such as one or more VOC sensors, and that manages the device 110's operations and interactions with respect to VOC detection and analysis functions.

With respect to informational data, e.g., program parameters and process data, this non-executable information can be referenced, manipulated, or written by the operating system or an application. Such informational data can include, for example, data that are preprogrammed into the device during manufacture, data that are created by the device or added by the user, or any of a variety of types of information that are uploaded to, downloaded from, or otherwise accessed at servers or other devices with which the device is in communication during its ongoing operation.

In an embodiment, a power supply 190, such as a battery or fuel cell, is included for providing power to the device 110 and its components. Additionally or alternatively, the device 110 may be externally powered, e.g., by a vehicle battery or other power source. In the illustrated example, all or some of the internal components communicate with one another by way of one or more shared or dedicated internal communication links 195, such as an internal bus.

In an embodiment, the device 110 is programmed such that the processor 140 and memory 150 interact with the other components of the device 110 to perform a variety of functions. The processor 140 may include or implement various modules (e.g., the software portions of the VOC module 180) and execute programs for initiating different activities such as launching an application, transferring data and toggling through various graphical user interface objects (e.g., toggling through various display icons that are linked to executable applications). As noted above, the device 110 may include one or more display screens 120. These may include one or both of an integrated display and an external display.

As noted above, a person's breath may be analyzed to determine carious things about the person. When a person breathes out, they emit a mixture of many chemicals and compounds including water, carbon dioxide ($CO^2$), aldehyde, sulfides, acetone, ammonia, ethanol and hydrogen. These various chemicals and compounds are VOC's (volatile organic compounds) as touched on briefly above.

Analysis of the relative amounts of these VOCs in a person's breath can be used to determine various health and wellness values for the person. For example, a high relative contribution from ethanol may indicate a state of alcohol impairment or intoxication, while a high relative contribution from volatile sulfur compounds (VSCs) can indicate that the person may be experiencing bad breath or halitosis. In addition, the VOCs in a person's breath can be analyzed to identify other conditions such as diabetes, kidney disease and lung disease.

As noted above, it is traditionally not practical to routinely monitor the VOC content of a person's exhalations, since specialized equipment is generally needed. People are unlikely to own or carry around with them such equipment. However, in an embodiment of the described principles, a system is provided wherein a VOC analysis module is included with (integrated into) or usable with (dockable onto) a mobile electronic communications device such as a mobile phone.

Figure 2A:
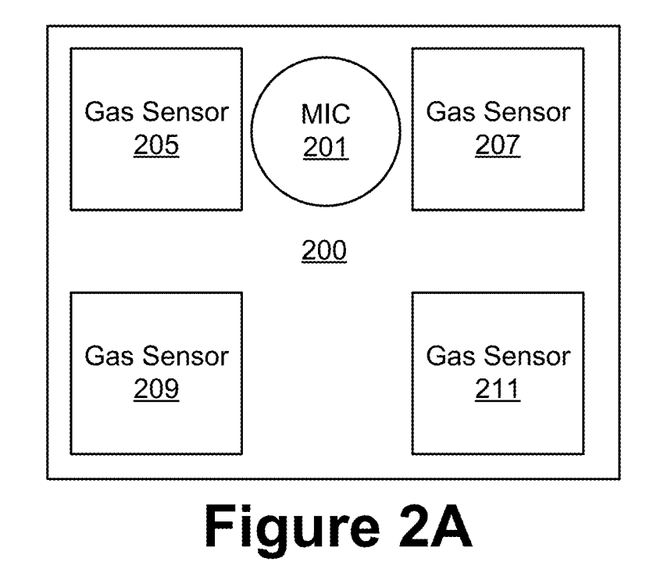
FIG. 2A is a schematic top view of hardware portions of a VOC module integrated with a device microphone in accordance with an embodiment of the disclosed principles.
Figure 2B:
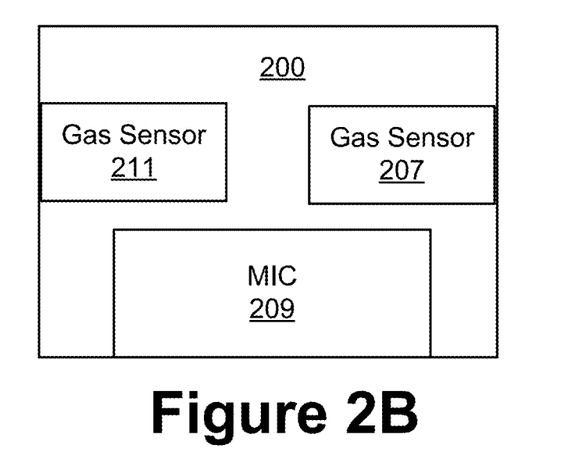
FIG. 2B is a schematic side view of hardware portions of a VOC module integrated with a device microphone in accordance with an embodiment of the disclosed principles.

FIG. 2 shows an example arrangement for such a device in the former embodiment, wherein certain hardware portions of the VOC module 180 are integrated with the device microphone. The figures show a cross-sectional top view and a cross-sectional side view respectively.

In the illustrated embodiment, the device microphone assembly 200 includes a number of gas sensors 205, 207, 209, 211 as well as a microphone 201 and a force sensor 203. Because they are in close proximity to the user's mouth while the user is speaking into the microphone 201, the gas sensors 205, 207, 209, 211 are able to sample the user's breath during each call or spoken interaction with the device. The force sensor 203 is positioned to detect any change in pressure (e.g., in PSI (pounds per square inch)) when the user is speaking into the microphone 201.

In operation, the VOC module 180 includes or employs a processor in low power (a low power core) to monitor VOCs. When the user is speaking, as detected by the force sensor 203, the low power core monitors the user's breath based on device context, e.g., the applications that are active (voice call, breath analysis, etc.), the user's voice level, and the pressure measured by the force sensor 203 located by the microphone 201.

If the device is inactive but has not been stowed or laid face down, the low power core monitors environmental air quality via the gas sensors 205, 207, 209, 211. In an embodiment of the described principles, when the device was not in use, e.g., the user is not speaking into the device, or when the device is stowed, e.g., is in the user's bag, pocket, purse or other container, the processor 140 causes periodic sampling of ambient environment VOC's by turning on the fan. In this embodiment, a pressure sensor reading is not needed to start the fan and initiate VOC sampling.

The accelerometer may be used to determine if the device is stationary and face up in order to monitor the environmental VOCs. This may be, for example, during the night with the device resting on a bed stand, at during the day when the device is on a desk, or plugged into a charger. If the device is moving, e.g., if it is being carried in the user's hand, the time interval for monitoring environmental VOCs may be adjusted based on distance traveled. For example, if the device is moving, more frequent sampling may be executed, since each sample may become obsolete as the environment changes.

Figure 3:
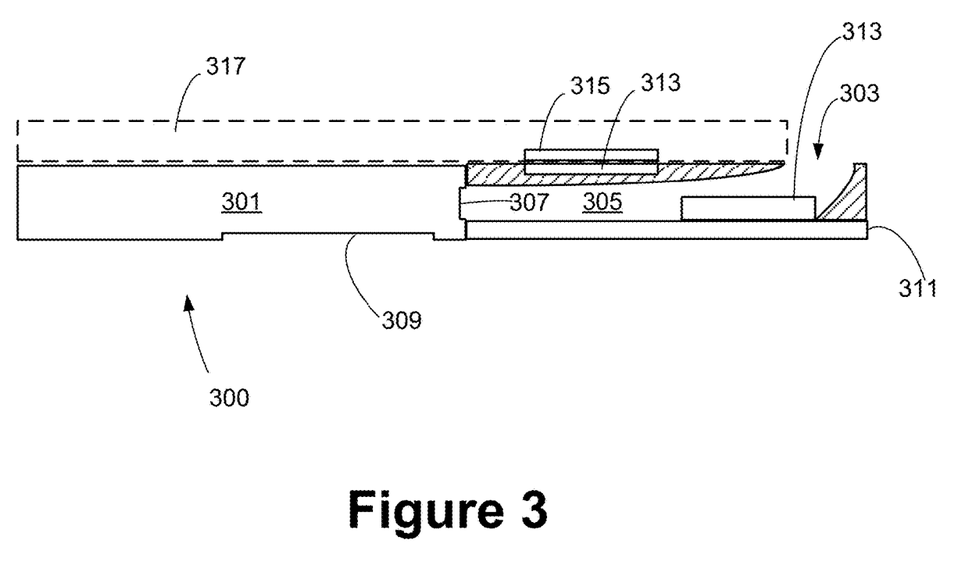
FIG. 3 is a schematic diagram of a VOC analysis module that is configured to be dockable to a mobile electronic communications device in accordance with an embodiment of the disclosed principles.

As noted above, the described principles can be implemented in an integrated design, an example of which is shown in FIG. 2, or may take the form of an add-on device configured to mate to another device, e.g., a mobile electronic communications device. Turning to FIG. 3, this figure shows an example of the latter approach, that is, an add-on device such as a MOTOROLA MOD module.

The illustrated module 300, shown in cross-section, includes a fan 301 for drawing air into an opening 303 via an internal passage 305 and fan inlet 307, and expelling the air from fan exhaust 309. A circuit board 311 such as a PCB (printed circuit board) for controlling the module 300 is located, in the illustrated embodiment, as the floor of the passage 305.

The module 300 is configured to mate to a mobile electronic communications device 317 such that the opening 303 extends past the lower edge of the electronic communications device 317 and can receive the user's breath. In this embodiment, the gas sensors 313 need not include or be accompanied by a microphone, since the microphone of the device 317 serves that purpose.

The module 300 may mate to and interact with the mobile electronic communications device 317 via an interface 313. A mating interface 315 on the rear of the mobile electronic communications device 317 completes the connection, allowing the module 300 and the device 317 to communicate data, control signals and other material. The module 300 may have its own power supply or may use the power supply of the mobile electronic communications device 317. Moreover, the module 300 may include its own processor (e.g., on PCB 311) and may use its processor solely or in conjunction with processor of the mobile electronic communications device 317.

In an optional embodiment, the module 300 includes a scoop (not shown) located over the opening 303. This serves to more efficiently direct the user's exhalations into the passage 305.

Figure 4A:
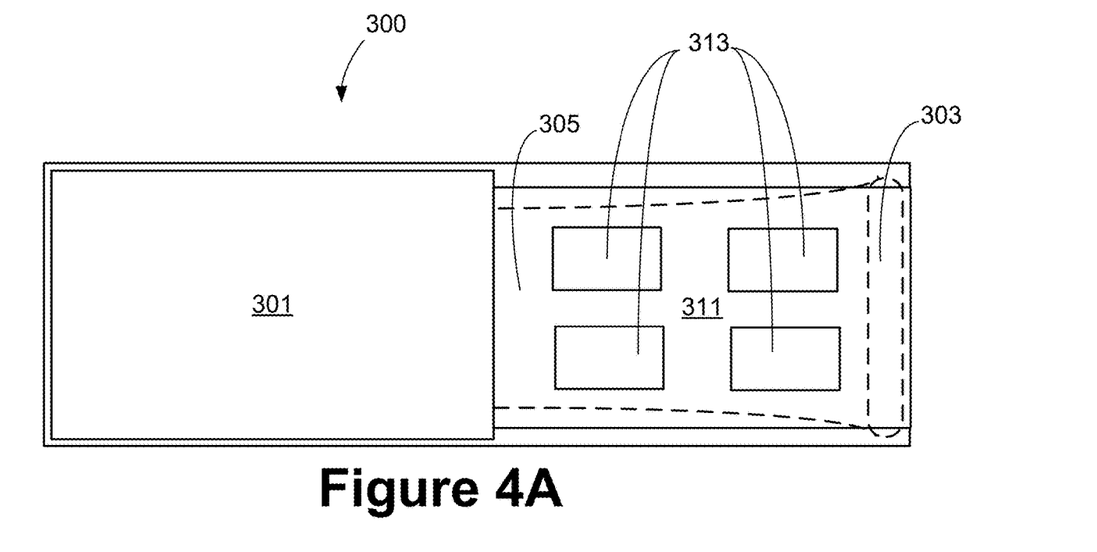
FIG. 4A is a schematic top view of a VOC analysis module in accordance with an embodiment of the disclosed principles.
Figure 4B:
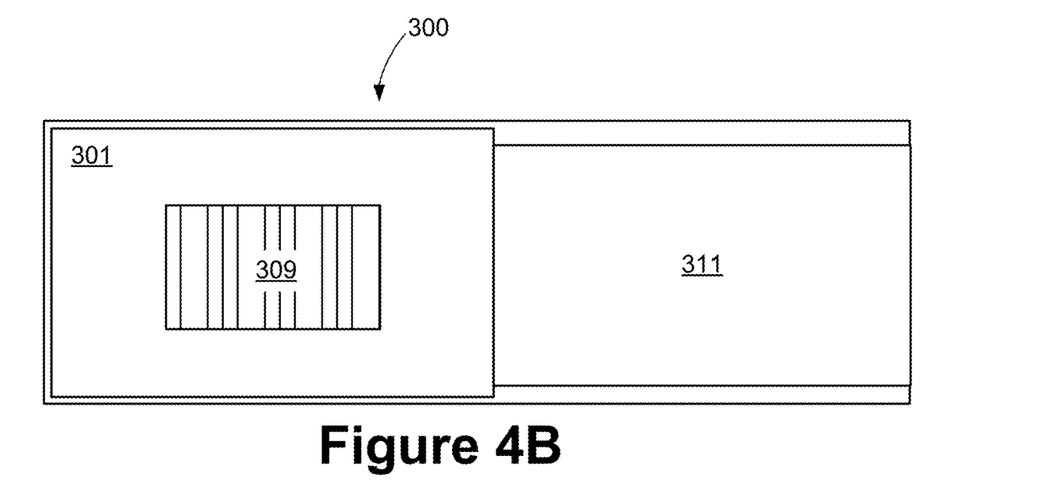
FIG. 4B is a schematic bottom view of a VOC analysis module in accordance with an embodiment of the disclosed principles.

FIGS. 4A and 4B show respective top and bottom schematic views of the module 300. As can be seen in the top view of FIG. 4A, the passage 305 may be as wide as the fan 301 or any other suitable width, and the opening 303 may include one large opening or, alternatively, multiple smaller openings. The passage preferably curves smoothly to minimize turbulence, but in an alternative embodiment may be more angularly shaped to aid impingement and dwell time of the incoming air on the sensors 313. The fan exhaust 309 can be seen in the bottom view of the module 300 as shown in FIG. 4B. It will be appreciated that although the fan exhaust 309 is shown as a rectangular grate or vent, any other suitable shape and configuration may be used, e.g., the exhaust 309 may be round, square, covered, open and so on.

Figure 5:
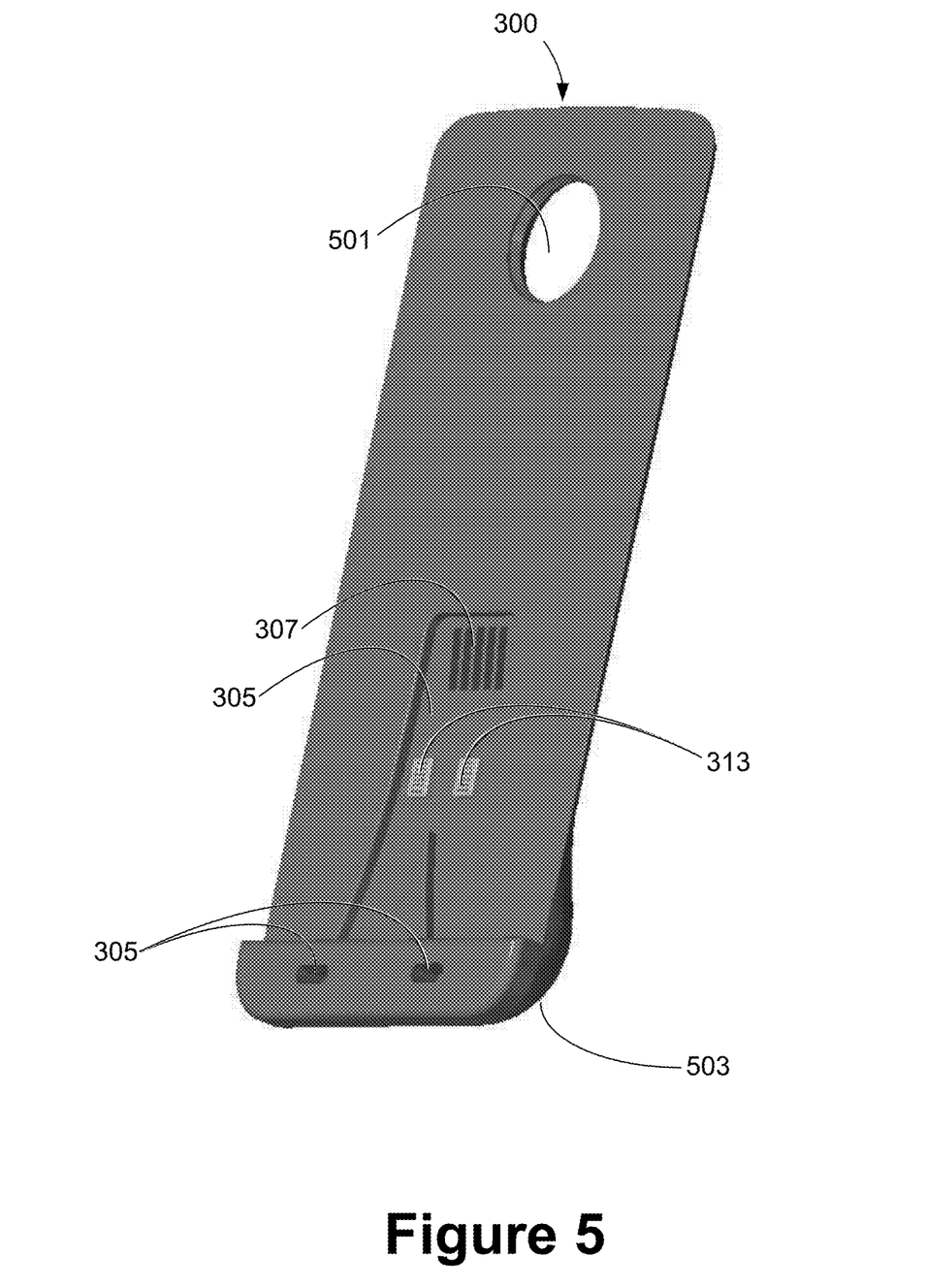
FIG. 5 is a perspective front view of a VOC analysis module in accordance with an embodiment of the disclosed principles.
Figure 6:
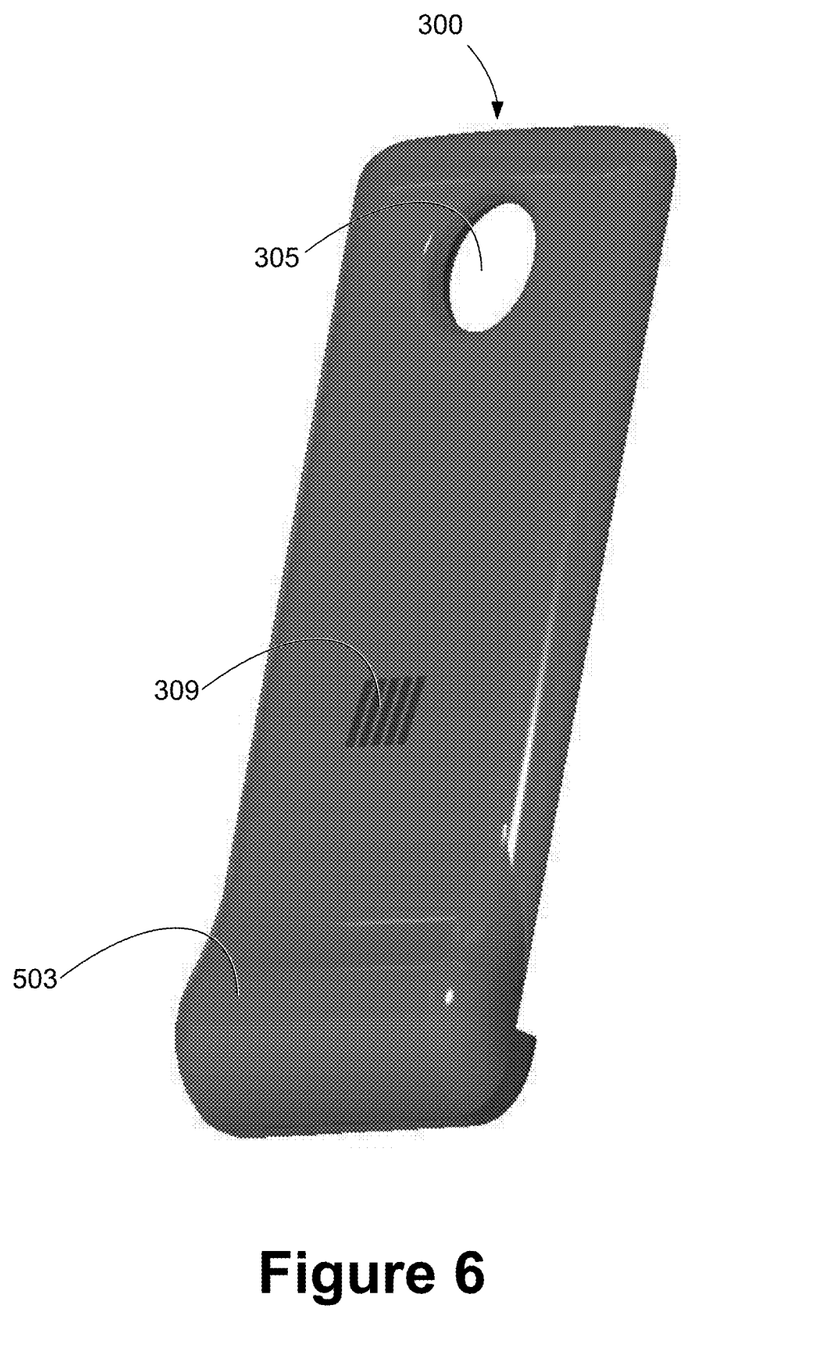
FIG. 6 is a perspective front view of a VOC analysis module in accordance with an embodiment of the disclosed principles.

In an embodiment, the module housing is of a smooth and sculpted form as shown in FIGS. 5 and 6. The material for the housing may be plastic, metal or other suitable material. Although the module 300 of FIGS. 5 and 6 is configured to mate to a mobile electronic communications device, not shown, the module 300 may not necessarily interact directly with such other device. If such interaction is needed or desired, a connector interface such as the interface 313 of FIG. 3 may be used.

FIGS. 5 and 6 show perspective front and rear views, respectively, of the module 300. In the illustrated embodiment, the top wall of the passage 305 is formed by a rear surface of the mobile electronic communications device 317 (not visible in this figure). An elastomeric seal, not shown, may be placed between the module 300 and the mobile electronic communications device 317 to reduce air loss from the passage 305.

The module 300 may include a camera hole 501 for fitting over a camera or lens assembly protruding from a mating device. Moreover, a scoop chin 503 may be included to more smoothly direct the user's exhalations to the fan intake 307. In this embodiment, two gas sensors 313 are located in the passage 305.

FIG. 6 shows a perspective back view of the module 300. In this view, the fan exhaust 309 and camera hole 501 can be seen. The shape of the scoop chin 503 may also be more easily seen in this figure. It will be appreciated that although the illustrated form is convenient and functional, other forms are certainly possible without departing from the scope of the described principles.

Figure 7:
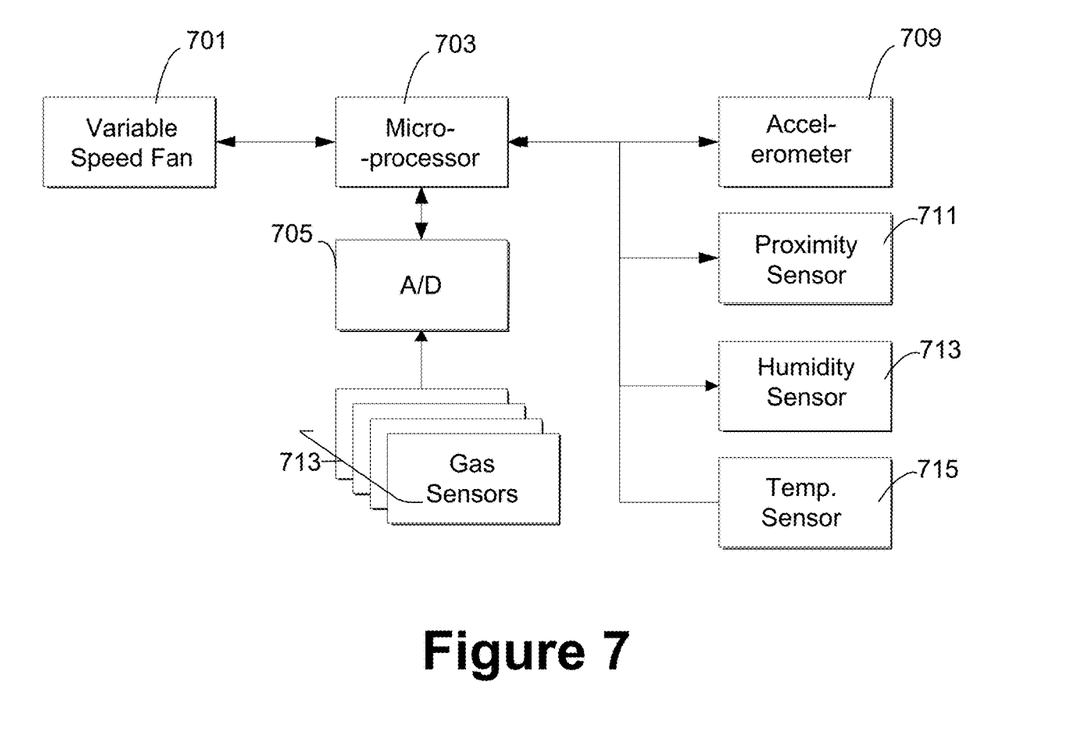
FIG. 7 is a schematic circuit diagram of a VOC analysis module in accordance with an embodiment of the disclosed principles.

Having described the structure and functional relationships of the module and its various components and counterpart devices, certain processes executed in an embodiment in support of the described functions will be described hereinafter. Turning to FIG. 7, this figure shows a schematic circuit view of the VOC module 180, with the understanding that various elements may be either dedicated to the VOC module 180 or shared, e.g., via the VOC module 180 mating to or being integrating with a mobile electronic communications device such as the device 110 of FIG. 1.

The VOC module 180 in the illustrated embodiment includes a variable speed fan 701 (e.g., FIG. 3, fan 301), one or more gas sensors 713 (e.g., FIG. 3, gas sensors 313), a microprocessor 703 and an analog-to-digital (A/D) converter 705. The microprocessor 703 is typically distinct from the host device 110 processor 140, but as noted above, the VOC module 180 shares the device processor 140 in an embodiment. The A/D converter 705 operates to digitize gas reading and provide them to the microprocessor 703.

A number of separate sensors are also provided to provide environmental and context information to the microprocessor 703. In the illustrated embodiment, these include an accelerometer 707, a proximity sensor 709, a humidity sensor 711 and a temperature sensor 713. The information from these sensors 707, 709, 711, 713 is usable by the microprocessor 703 to better analyze incoming gas data. For example, a gas reading in humid air may show a lower ethanol content in a user's breath for the same blood alcohol level.

Figure 8:
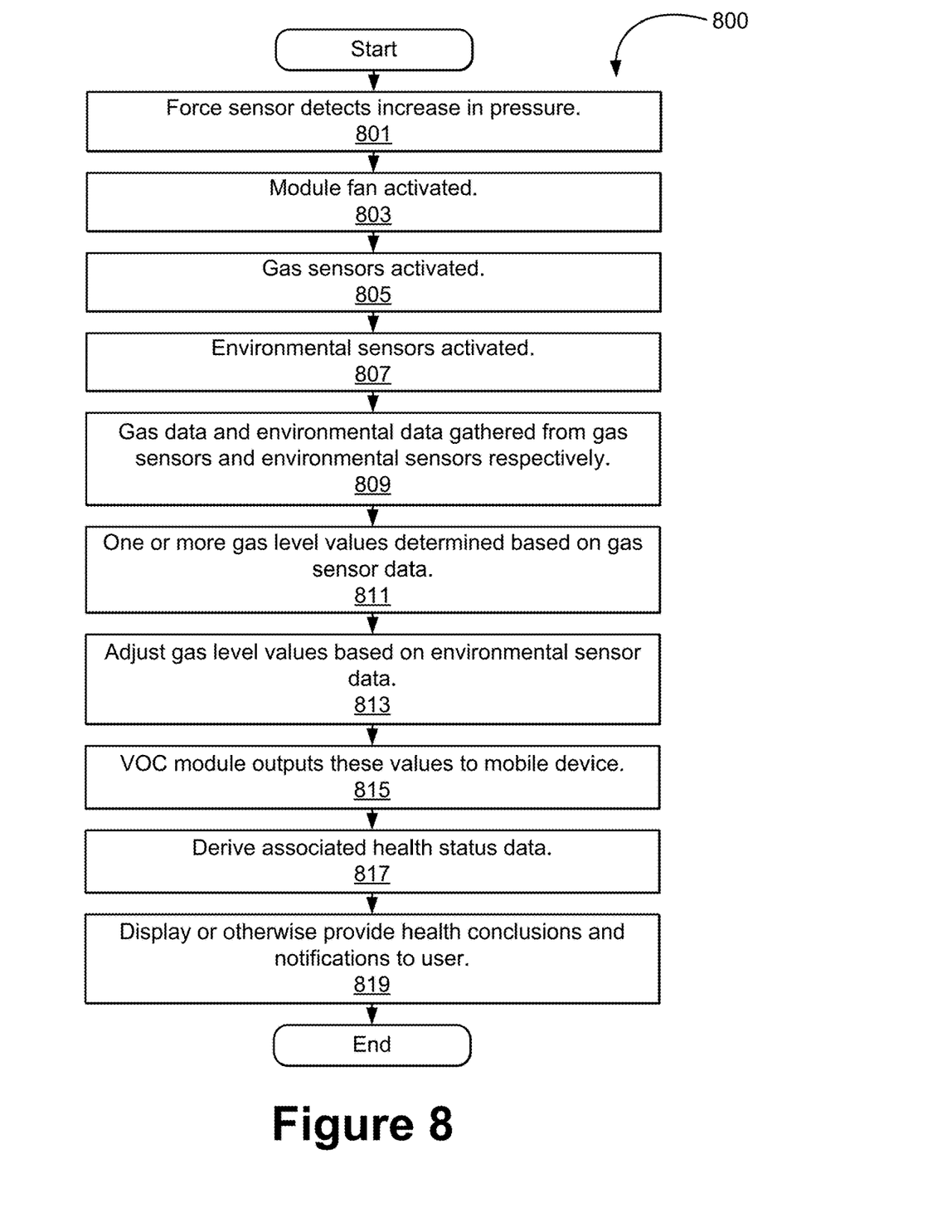
FIG. 8 is a flow chart showing an example process of user breath analysis in accordance with an embodiment of the disclosed principles.

The operation of the system in an example embodiment may be more fully understood from the flow chart of FIG. 8. While the illustrated steps are taken by the VOC module 180 microprocessor 703 in an embodiment, it will be appreciated, as discussed above, that another processor, such as the mobile device processor, may execute all or some of the steps.

The illustrated process 800 begins with the detection, by a force sensor such as force sensor 203 in FIG. 2, of an increase in pressure at stage 801, corresponding to a user speaking into or close to the device microphone. The module fan, e.g., fan 301, is then activated at stage 803. Contemporaneously at stage 805, one or more gas sensors, e.g., one or more of sensors 313, may be activated if they are not already powered. Similarly, at stage 807, one or more environmental sensors, e.g., sensors 709-715, may also be activated.

At stage 809, gas data is gathered from the one or more gas sensors and environmental data is gathered from the one or more environmental sensors, and at stage 811, one or more gas level values are determined based on the gas sensor data. The one or more gas level values may then be adjusted at stage 813 based on the environmental sensor data. For example, ambient temperature and pressure may be used to calibrate a sensed ethanol level to its sea-level equivalent.

Having calculated the calibrated levels of various gases in the user's exhalation, the VOC module 180 outputs these values to the mated mobile electronic communications device at stage 815, whereupon the mobile electronic communications device may derive associated health status data at stage 817 and display or otherwise provide associated health conclusions and notifications to the user at stage 819. Alternatively, stage 815 may be skipped and the VOC module 180 may itself execute one or both of stages 817 and 819.

It will be appreciated that various systems and processes have been disclosed herein. However, in view of the many possible embodiments to which the principles of the present disclosure may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

We claim:

1. A mobile communications device accessory comprising:
   an accessory housing shaped to mate to a mobile communications device in a mated position, the accessory housing having an opening therein to admit an exhalation of a user of the device while the user is speaking;
   a passageway internal to the device housing and connected to the opening, the passageway having a fan inlet linked to the passageway to draw air into the passageway from the opening;
   at least one gas sensor within the passageway, located such that a user exhalation entering the opening will impinge on the at least one gas sensor, the at least one gas sensor providing an output indicative of an amount of a sensed gas; and
   an electrical interface located to mate with a corresponding interface on the mobile communications device when the accessory housing is in the mated position.

2. The mobile communications device accessory according to claim 1, further including a processor communicably linked to the at least one gas sensor, and configured to receive the output of the at least one gas sensor, generate user biological information based on the output and provide the user biological information to the mobile communications device via the electrical interface.

3. The mobile communications device accessory according to claim 2, wherein the biological information includes information associated with one or more of user blood alcohol level, user halitosis, user $CO^2$ level, user diabetes, user lung disease and user kidney disease.

4. The mobile communications device accessory according to claim 1, further including a processor communicably linked to the at least one gas sensor to receive the output of the at least one gas sensor and provide a signal based on the output to the mobile communications device via the electrical interface.

5. The mobile communications device accessory according to claim 1, wherein the at least one gas sensor comprises multiple gas sensors.

6. The mobile communications device accessory according to claim 5, wherein the multiple gas sensors are configured to detect volatile organic compounds (VOCs) including one or more of water, carbon dioxide ($CO^2$), aldehyde, sulfides, acetone, ammonia, ethanol and hydrogen.

7. The mobile communications device accessory according to claim 1, further comprising a force sensor adjacent the opening, the force sensor outputting a pressure signal related to incoming air pressure.

8. The mobile communications device accessory according to claim 7, wherein the accessory is further configured to activate the at least one gas sensor based on the pressure signal.

9. The mobile communications device accessory according to claim 7, wherein the processor is further configured to activate the at least one gas sensor absent a pressure signal from the force sensor when the device is detected to be stationary and face up.

10. The mobile communications device accessory according to claim 1, wherein the processor is further configured to cause the generated biological information to be shown via a display of the mobile communications device.

11. The mobile communications device accessory according to claim 1, further comprising a fan outlet, the fan outlet being positioned to expel air from the passageway.

* * * * *